United States Patent [19] [11] 4,080,377
Block et al. [45] Mar. 21, 1978

[54] PRODUCTION OF CYCLIC FIVE-MEMBERED RING UNSATURATED PHOSPHINE DICHLORIDES

[75] Inventors: Hans-Dieter Block; Reinhard Schliebs, both of Cologne, Germany

[73] Assignee: Bayer Aktiengesellschaft, Leverkusen, Germany

[21] Appl. No.: 766,418

[22] Filed: Feb. 7, 1977

[30] Foreign Application Priority Data

Feb. 19, 1976 Germany ............................. 2606682

[51] Int. Cl.² ........................... C07F 9/34; C07F 9/53
[52] U.S. Cl. ........................... 260/543 P; 260/329 P; 260/606.5 P
[58] Field of Search ................. 260/329 P, 606.5 P, 260/543 P

[56] References Cited

U.S. PATENT DOCUMENTS

| 2,268,157 | 12/1941 | Marvel | 260/543 P X |
| 2,663,736 | 12/1953 | McCormack | 260/606.5 P |
| 2,663,737 | 12/1953 | McCormack | 260/606.5 P |
| 2,663,738 | 12/1953 | McCormack | 260/606.5 P |
| 2,693,482 | 11/1954 | Stayner | 260/543 P |
| 2,694,684 | 11/1954 | Rogers et al. | 260/606.5 P X |
| 2,871,263 | 1/1959 | Short | 260/543 P |
| 3,723,520 | 3/1973 | Smith et al. | 260/543 P |
| 3,737,456 | 6/1973 | Smith et al. | 260/543 P |
| 3,751,460 | 8/1973 | Schliebs et al. | 260/543 P |
| 3,855,186 | 12/1974 | Moedritzer | 260/606.5 P X |

FOREIGN PATENT DOCUMENTS 186,465   10/1966   U.S.S.R.

OTHER PUBLICATIONS

Hasserodt et al., Tetrahedron, V19, pp. 1563, 1568 and 1573 (1963).

*Primary Examiner*—Helen M. S. Sneed
*Attorney, Agent, or Firm*—Burgess, Dinklage & Sprung

[57] ABSTRACT

In the production of isomeric five-membered ring cyclic unsaturated phosphine dichlorides by reacting an organophosphorus dichloride with a diene, the improvement which comprises carrying out the reaction in a carboxylic acid chloride. The product, without isolation, can be directly used in reaction with the carboxylic acid anhydride corresponding to the acid chloride to produce the phosphine oxide, the reaction producing additional acid chloride from the anhydride.

7 Claims, No Drawings

PRODUCTION OF CYCLIC FIVE-MEMBERED RING UNSATURATED PHOSPHINE DICHLORIDES

This invention relates to a process for the production of isomeric five-membered cyclic unsaturated phosphine dichlorides using carboxylic acid chlorides as solvent.

The possibility of reacting halides of trivalent phosphorus with 1,3-dienes to form five-membered cyclic unsaturated phosphine dihalides has long been known. If carried out in the absence of solvents, however, the reaction is very slow. According to U.S. Pat. No. 3,751,460, oxy halides of 5-valent phosphorus are proposed as solvents for the reaction and in this way, substantially pure end products are obtained in high yields and by a relatively fast reaction. Attempts have also been made further to accelerate the reaction between 1,3-dienes and organodihalogen phosphines using nitrobenzene and other nitrohydrocarbons as solvent (U.S. Pat. No. 3,855,186). Unfortunately, mixtures of strong reducing agents, such as organodichlorophosphines and organic nitro compounds which have an oxidizing effect under suitable conditions are not entirely safe to handle. Accordingly, this proposal (U.S. Pat. No. 3,855,186) is not a practical alternative to carrying out the reaction in oxy halides of phosphorus as solvent. It has also been proposed (cf. Russian Patent Specification No. 186,465) to use acetic acid anhydride as solvent for this reaction. Unfortunately, this proposal is not practical either, because organodihalogen phosphines react quickly with acetic acid anhydride (Russian Patent Specification No. 186,465). However, the use of the oxy halides of 5-valent phosphorus, especially phosphorus oxy chloride, involves certain disadvantages which are discussed hereinafter. Normally the five-membered cyclic phosphine dihalides are only intermediate products for the production of the five-membered cyclic phosphine oxides. Before this conversion can be carried out, for example by hydrolysis, the oxy halides of 5-valent phosphorus used as solvent has to be removed as completely as possible, for example by distillation, decantation or filtration, because the oxy halides of 5-valent phosphorus form very stable complexes with the five-membered cyclic phosphine oxides. Recovery of the five-membered cyclic phosphine oxides from these complexes is only possible by total hydrolysis with greatly increased outlay in terms of chemicals, time and space for working up, especially for neutralization, and with increased production both of salts of the associated phosphorus/oxygen acid and of metal halide. Even if the oxy halides of five-valent phosphorus used as solvent are removed as completely as possible, which involves a considerable amount of time, part of the solvent remains trapped in the solid crystalline five-membered cyclic phosphine dihalide. In addition to the disadvantages referred to above, there is the further disadvantage that, following neutralization, extraction of the five-membered cyclic phosphine oxide is impeded by the substantially insoluble salts, trisodium phosphate and disodium phosphate. In addition, the large amount of solvent trapped in the five-membered cyclic phosphine dihalide is lost.

If, in addition, an attempt is made to obtain the halogen bonded in the five-membered cyclic phosphine dihalides in the form of valuable acid halides or versatile alkyl halides, rather than in the form of almost worthless hydrogen halide or in the form of an aqueous solution thereof, the presence of readily volatile solvents, for example phosphorus oxy chloride or methane phosphonic acid dichloride, which are only liberated during working up, again makes itself felt in the form of an undesirable phosphorus content in the halogen-containing end products obtained.

Accordingly, the object of the present invention is to provide a process for reacting 1,3-dienes with halides of 3-valent phosphorus to form five-membered cyclic unsaturated phosphine dihalides, which has the advantage associated with working in reaction-accelerated phosphorus-(V)-oxide halide solvents, but avoids the disadvantages referred to above. Accordingly, the present invention relates to a process for the production of isomeric pentacyclic unsaturated phosphine dichlorides by reacting organo phosphorus dichlorides with dienes, optionally in the presence of conventional polymerization inhibitors, characterized by the fact that the reaction is carried out in carboxylic acid chlorides.

It has surprisingly been found that the reaction of 1,3-dienes with organodichlorophosphines in carboxylic acid chlorides as solvent proceeds quickly and with high yields to produce five-membered cyclic unsaturated phosphine dichlorides corresponding to the formulae:

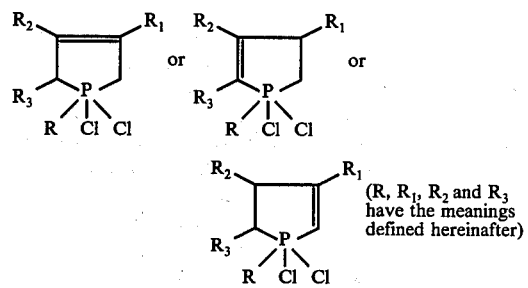

(R, R$_1$, R$_2$ and R$_3$ have the meanings defined hereinafter)

A number of other acid chlorides and acid-chloride-like chlorides, for example boric acid chloride, titanium tetra-chloride, tin tetrachloride (stannic acid chloride), sulfuryl chloride (sulfuric acid dichloride), phosphorus trichloride (phosphorus acid trichloride), organo phosphorus chlorides (phosphonous and phosphinous acid chlorides), antimony trichloride (antimonous acid chloride), sulfur dichloride and disulfur dichloride, cannot be used as solvents for the reaction of organodichlorophosphine and 1,3-diene on account of troublesome secondary reactions. Other acid chlorides similar to the carboxylic acid chlorides are unsuitable for use as solvents on account of their unfavorable boiling points or melting points, for example phosgene (carbonic acid chloride) and sulfonic acid chlorides.

In contrast to the unsaturated five-membered cyclic phosphine dihalides obtained by the process according to Patent 3,751,460, the unsaturated five-membered cyclic phosphine dichlorides obtained by the process according to the present invention do not necessitate removal of the solvent used for the reaction before they are further processed into the five-membered cyclic phosphine sulfides and oxides.

The suitability of the carboxylic acid chlorides as non-complexing solvents is also surprising insofar as it is already known that acid chlorides and acid-chloride-like metal halides form complexes with five-membered cyclic unsaturated phosphine oxides (cf. German Offenlegungsschrift No. DOS 2,245,634). Acid chlorides, which form addition compounds with the unsaturated five-membered cyclic phosphine oxides, very frequently contain elements which are adjacent to carbon in the Periodic System of Elements, for example S, P, As, Si, Sn and B. Representatives include boron trichloride, alkyl and aryl boron dichlorides, aluminum trichloride, organyl aluminum dichlorides, diorganyl aluminum chlorides, silicon tetrachloride, methyl trichlorosilane, dimethyl dichlorosilane, tin tetrachloride, organo tin chlorides, phosphorus trichloride, methyl dichlorophosphine, phosphorus oxychloride, methane phosphonic acid dichloride, 1-chloro-1-oxophospholene, antimony-(V)-chloride, thionyl chloride, sulfuryl chloride, methane sulfonic acid chloride and p-toluene sulfonic acid chloride.

However, one major advantage of using carboxylic acid chlorides as the solvent is that they do not form any complexes with 5-membered cyclic phosphine oxides. Carboxylic acid chlorides as solvents also increase the safety of the process because, in the presence of water, for example from heating or cooling media, a much smaller amount of heat is evolved than in cases where phosphoryl chlorides, for example phosphorusoxychloride, are present. In addition, the toxicity of the carboxylic acid chlorides is also distinctly lower than that of the phosphorus oxychlorides, as also reflected in the MAK-values for acetyl chloride and phosphorus oxychloride.

The 5-membered cyclic unsaturated phosphine dichlorides may be further processed, for example to form the phosphine oxides, by reaction with oxygen donors known per se with the structure R—O—H (cf. U.S. Pat. No. 2,663,737), for example water, alcohols, and carboxylic acids, and also with carboxylic acid esters, acetals, ketals, ketones, orthocarbonic acid esters, orthocarboxylic acid esters, alkylene-1,2-oxides, alkylene-1,3-oxides, and preferably by reaction with the acid anhydride associated with the carboxylic acid chloride used as solvent. In this case, the chlorine bonded in the 5-membered cyclic phosphine dichlorides is completely recovered in the form of valuable carboxylic acid chloride.

When the other above-mentioned oxygen donors are used for converting the 5-membered cyclic phosphine dichlorides, alkyl chlorides, carboxylic acid chlorides, mixed dichloroalkanes, α,β-dichloroalkanes and α,γ-dichloroalkanes are obtained as useful products in addition to hydrogen chloride. Apart from water, suitable oxygen donors are, for example, methanol, ethanol, isopropanol, 2-ethyl hexanol, formic acid, acetic acid, propionic acid, benzoic acid, methyl acetate, methyl formate, methyl benzoate, phthalic acid dimethyl ester, formaldehyde dimethyl acetal, acetaldehyde dimethyl acetal, acetone dimethyl ketal, orthocarbonic acid tetramethyl ester, orthocarbonic acid tetraethyl ester, orthoformic acid trimethyl ester, ethylene oxide, propylene oxide, i-butylene oxide, butene-2,3-oxide, acetanhydride, propionic acid anhydride, benzoic acid anhydride, maleic acid anhydride, phthalic acid anhydride and ketene.

The 5-membered cyclic phosphine oxide is obtained by any one of various methods known per se according to the particular oxygen donor used for production from the 5-membered cyclic phosphine dichloride. Oxygen donors containing active hydrogen atoms always give hydrogen chloride as one reaction product when reacted with 5-membered cyclic phosphine dichlorides. Since hydrogen chloride forms stable complexes with the 5-membered cyclic phosphine oxides, neutralization has to be carried out before isolation of the phosphine oxide. Details of the working up techniques may be found, for example, in U.S. Pat. Nos. 2,663,736; 2,663,737; and 2,663,738. If, by contrast, oxygen donors without any active hydrogen atoms of the kind mentioned above are used, separation may be carried out directly without any further auxiliary operations, for example by distillation.

The use of the acid anhydride associated with the carboxylic acid chloride used as solvent affords particular advantages because in that case the solvent and reaction product are identical with one another so that there is no need for any separation work. Naturally the solvent trapped during synthesis in the crystalline 5-membered cyclic phosphine dichlorides also has no adverse effect upon conversion of the phosphine dichloride into the phosphine oxide because the solvents used in both stages of the reaction are the same and free from phosphorus and are quantitatively recovered. In this way, a phosphorus-free carboxylic acid chloride is obtained as useful product in the addition of the 5-membered cyclic phosphine oxide.

In one preferred embodiment of the process according to the invention, an organophosphorus dichloride corresponding to the formula

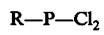

in which R represents an optionally substituted aliphatic, cycloaliphatic, aromatic or araliphatic radical, is reacted with a diene corresponding to the formula

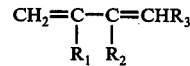

in which the radicals $R_1$, $R_2$ and $R_3$ may be the same or different and represent hydrogen, chlorine, an alkyl radical with 1 to 4 carbon atoms or phenyl, in the presence of conventional polymerization inhibitors in a carboxylic acid chloride as solvent at a temperature in the range from 20° to 90° C.

In the context of the invention, aliphatic radicals are alkyl radicals with 1 to 18 carbon atoms, preferably with 1 to 4 carbon atoms, and also cycloaliphatic radicals with 5 to 12 carbon atoms, preferably with 5, 6 or 7 carbon atoms in the ring system. These aliphatic radicals may optionally be substituted by halogen atoms (preferably fluorine, chlorine or bromine). Optionally substituted aromatic radicals are the naphthyl radical, but preferably the phenyl radical. The araliphatic radicals (R) contain from 1 to 4 carbon atoms and preferably 1 or 2 carbon atoms in the aliphatic chain, the preferred aromatic radical being the phenyl radical. Substituents of the aromatic and araliphatic radicals are halogen atoms (preferably fluorine, chlorine, bromine) and/or lower alkyl radicals with 1 to 4 carbon atoms. The cycloaliphatic radical may also be optionally substituted by such lower alkyl radicals.

Dienes preferably used for the process according to the invention are dienes in which the radicals $R_1$, $R_2$ and $R_3$ represent hydrogen and also hydrogen and methyl. Suitable compounds of the formula $RPCl_2$ are compounds such as methyl dichlorophosphine, ethyl dichlorophosphine, butyl dichlorophosphine, 2-chloroethyl dichlorophosphine, chloromethyl dichlorophosphine, trichloromethyl dichlorophosphine, cyclohexyl dichlorophosphine, phenyl dichlorophosphine, naphthyl dichlorophosphine and thienyl dichlorophosphine.

Examples of suitable dienes are butadiene, isoprene, dimethyl butadiene, chloroprene, 1-methyl butadiene, 1-phenyl butadiene.

The carboxylic acid chlorides used as solvents are alkane carboxylic acid chlorides, preferably those with lower hydrocarbon radicals containing from 2 to 4 carbon atoms, halogen alkane carboxylic acid chlorides, in which the halogen atoms fluorine, chlorine and/or bromine are attached to the alkyl radical, aryl carboxylic acid chlorides, in which the phenyl ring may be substituted by alkyl radicals with 1 to 4 carbon atoms or by the halogens fluorine, chlorine and/or bromine, aralkane carboxylic acid chlorides which may be substituted by alkyl radicals or by halogen atoms, and also aromatic and aliphatic dicarboxylic acid dichlorides. Examples of such carboxylic acid chlorides are acetyl chloride, propionic acid chloride, butyric acid chloride, chloroacetyl chloride, bromoacetyl chloride, β-chloropropionic acid chloride, benzoyl chloride, p-chlorobenzoyl chloride, m-isopropyl benzoyl chloride, phenylacetyl chloride, succinic acid dichloride and phthaloyl dichloride.

The process according to the invention may be carried out at temperatures in a relatively wide range. Generally, the process according to the invention is carried out at temperatures in the range from 20° to 90° C and preferably at temperatures in the range from 40° to 80° C, allowance naturally being made for the reactivity of the particular reaction components. The duration of the reaction is also governed by the reactivity of the components. It may amount to between a few hours and a few days and preferably to between 20 hours and 120 hours. The atmosphere prevailing over the reaction mixture may consists of an inert gas or, preferably, completely of the vapors of the solvent and the reactants used.

The process according to the invention may be carried out under normal pressure or at elevated pressure and, in some cases, even at subatmospheric pressure. It may be necessary to work under pressure in cases where the dienes used are gaseous at the reaction temperature, such as butadiene. The pressure spontaneously adjusted in the reaction vessel corresponds to the vapor pressure of the components at the temperature prevailing in the particular mixing ratio applied.

The ratio of solvent to the sum total of reactants may be varied within a relatively wide range. Although ratios (in parts by weight) of about 5 to 1 (solvent: sum total of reactants) give good yields, the necessary recovery of the solvent does involve considerable outlay. On the other hand, ratios of about 1 to 1 (solvent: sum total of reactants), although again giving useful results, are not very suitable in the case of highly reactive dienes on account of the danger of a spontaneous reaction and the resulting problem of heat dissipation. Particularly favorable conditions in regard to the above-mentioned factors are obtained when the ratio of solvent to the sum total of the reactants amounts to between about 1.5:1 and about 3:1.

It is known that it is best to add polymerization inhibitors during the reaction between organodihalogen phosphines and dienes (cf. Houben-Weyl, Methoden der org. Chemie, 1963, Vol. XIV, 1). In the process according to the invention, too, it is best to add inhibitors, for example copper stearate, phenothiazines or tert.-butyl pyrocatechol, in quantities of from about 0.1 to 1.0% by weight, based on the sum total or organodihalogen phosphine and diene. Production of the 5-membered cyclic phosphine dichlorides may be carried out either continuously or in batches. In view of the normally relatively long reaction times, batch operation may generally be used. The reaction components may be added either simultaneously or successively to the solvent. In the case of dienes which are not too active, such as for example butadiene, it is readily possible simultaneously to heat the reactants in the carboxylic acid chloride. In the case of more active dienes (for example isoprene), it may be advisable to add the diene to the mixture of carboxylic acid chloride and organodichlorophosphine. On the other hand, however, it is also possible to add the organodichlorophosphine to a mixture of carboxylic acid chloride and diene, or to add the diene and organodichlorophosphine simultaneously to the solvent. The two reactants, the organodichlorophosphine and the diene, are best used in a molar ratio of approximately 1:1 for the reaction but it is also possible to use an excess of one of the two components. Which of the two components is used in excess will generally depend on whether the diene or the organophosphorus dichloride is the more readily obtainable, so that the readily obtainable dienes (butadiene, isoprene or 2-chlorobutadiene) may be used in excess. On completion of the reaction, the excess diene may be separated off from the reaction mixture by distillation.

Depending upon the particular method selected for working up, the phosphine dichloride formed is either free from the solvent added by the methods already explained or alternatively is further reacted in the presence of this solvent. The compounds obtained by the process according to the invention are valuable intermediate products for the production of the corresponding oxides or sulfides which are inter alia valuable catalysts for carbodiimide-forming reactions.

The process according to the invention is illustrated by the following Examples.

EXAMPLE 1 (Comparison Example)

234 g of methyl dichlorophospholine and 450 ml of phosphorus oxychloride are mixed together. 150 g of isoprene are introduced into the resulting solution and the reaction mixture is left standing for 10 days at 20° to 21° C. Thereafter phosphorus oxychloride and unreacted reactants are distilled off in vacuo, the temperature of the distillation residue being kept below 50° C. The residual crystalline sludge of 1,3-dimethyl-1,1-dichlorophospholine is hydrolyzed with effective external cooling by the careful, dropwise addition of water, and the homogeneous aqueous solution is neutralized by the addition of 50% sodium hydroxide and then diluted with water to a total volume of 750 ml. The 1,3-dimethyl-1,1-oxophospholine is extracted from this solution containing sodium chloride, 1,3-dimethyl-1-oxophospholine and also undissolved, suspended disodium hydrogen phosphate by extraction four times with 800 ml of chloroform. Removal of the chloroform from the combined chloroform extracts by distillation leaves behind 111 g of 1,3-dimethyl-1-oxophospholine (42.8% of the theoretical yield).

EXAMPLE 2 the production of 1,3-dimethyl-1-oxophospholine in accordance with Example 1 is repeated with the difference that 450 ml of acetyl chloride are used as solvent instead of the phosphorus oxychloride. The size of the batch, the reaction conditions and working up remain the same. The neutralized hydrolysis solution is homogeneous. 1,3-Dimethyl-1-oxophospholine is left as residue in a quantity of 148 g (57% of the theoretical yield).

Comparision of Examples 1 and 2 shows that, even under non-optimal conditions, the main reaction is accelerated to a greater extent by the use of acetyl chloride as solvent than by the use of phosphorus oxychloride.

EXAMPLE 3

150 g of isoprene are introduced into a mixture of 234 g of methyl dichlorophosphine and 450 ml of benzoyl chloride. The reaction mixture is left standing for 10 days at 20° to 21° C. Thereafter benzoyl chloride and unreacted starting materials are distilled off in a vacuum of 1 mm Hg, the temperature of the distillation residue being kept below 50° C. The residual crystals of 1,3-dimethyl-1,1-dichlorophospholine are hydrolyzed by the gradual dropwise addition of water with intensive external cooling.

Shaking once with 300 ml of methylene chloride completely removes small quanitites of benzoic acid formed by the hydrolysis of adhering benzoyl chloride. The hydrolysis solution is neutralized with sodium hydroxide and made up with water to 750 ml. The 1,3-dimethyl-1-oxophospholine is isolated from the neutral solution in the same way as in Example 1. Yield: 109 g of 1,3-dimethyl-1-oxophospholine (41.9% of the theoretical yield).

EXAMPLE 4

The production of 1,3-dimethyl-1-oxophospholine in accordance with Example 3 is repeated with the difference that 450 ml of succinic acid dichloride are used instead of the benzoyl chloride. The solvent is removed at 0.2 mm Hg, the other conditions remain unchanged. The yield comprises 112 g of 1,3-dimethyl-1-oxophospholine (43% of the theoretical yield).

Under the external conditions of Examples 1 and 2, therefore, other carboxylic acid chlorides (Examples 3 and 4) also give reaction results which are equivalent or even better to those obtained in cases where phosphorus oxychloride is used as solvent.

EXAMPLE 5

702 g of methyl dichlorophosphine, 1350 ml of acetyl chloride and 450 g of butadiene are mixed under dry nitrogen at −20° C and the resulting mixture is introduced into an enamelled stirrer-equipped autoclave. After the autoclave has been closed, the stirred mixture is heated to 50° C and left standing at that temperature for 73 hours. The pressure inside the autoclave falls from 2.2 atmospheres gauge to 1.9 atmospheres gauge after 24 hours and finally to 1.8 atmospheres gauge. Thereafter the contents of the autoclave are cooled, the autoclave is opened and its contents removed. The liquid fractions are decanted off from the white crystals precipitating. Drying in vacuo (50° C/1 mm Hg) leaves 970 g of 1-methyl-1,-dichlorophospholine in the form of white crystals (95% of the theoretical yield). After hydrolysis and neutralization, the aqueous phase is extracted five times with 1 liter of chloroform. 548 g of 1-methyl-1-oxophospholine (78.7% of the theoretical yield, based on the methyl dichlorophosphine used) are isolated from the combined chloroform extracts by concentration.

EXAMPLE 6 (Comparison with Example 5)

The procedure is as described in Example 5, except that 1350 ml of phosphorus oxychloride are used instead of the acetyl chloride. At a reaction temperature of 50° C, the pressure falls from 1.5 atmospheres gauge to 0.9 atmospheres gauge after 24 hours, to 0.5 atmosphere gauge after 48 hours and finally to 0.3 atmosphere gauge after 73 hours. Working up is carried out in the same way as in test 6. However, the neutralized hydrolysis solution contains suspended disodium hydrogen phosphate. The yield of 1-methyl-1-oxo phospholine amounts to 537 g (77.1% of the theoretical yield), based on the methyl dichlorophospholine used). Recovery of the phosphorus oxychloride used amounts to 2140 g (94.8% of the input).

EXAMPLE 7

The procedure is as described in Example 6. After a reaction time of 73 hours at 50° C, the reaction mixture is cooled and transferred to a glass apparatus equipped with a stirrer and a distillation column. 930 g of aceticanhydride are then added and the temperature of the reaction mixture is initially raised to 50° C. After some first runnings, acetyl chloride is removed through the column for a reflux ratio of 2:1. When the sump temperature reaches 90° C, it is kept at that temperature for another 4 hours.

No more acetyl chloride distills off during the last 2.5 hours. In order completely to remove acetyl chloride, the pressure is slowly reduced to approximately 80 mm Hg for the same sump temperature, the residue of unreacted aceticanhydride beginning to distil. The total quantity of distilled acetyl chloride amounts to 2415 g, i.e. the total quantity of the acetyl chloride used as solvent plus the acetyl chloride formed from acetyl hydride in a yield of 98% of the theoretical yield, based on the methyl dichlorophospholine used. No phosphorus can be detected in the acetyl chloride. The recovery of aceticanhydride, which is distilled off in vacuum from the residual solution, amounts to 213 g, corresponding to 96% of the quantity of aceticanhydride theoretically expected after deduction of the quantity converted into acetyl chloride. The residue is diluted with 100 ml of water, neutralized by the addition of sodium hydroxide and then extracted twice with 1 liter of chloroform. The yield of 1-methyl-1-oxophospholine from the chloroform extracts amounts to 503 g (74.5% of the theoretical yield).

EXAMPLE 8

702 g of methyl dichlorophosphine, 1350 ml of phosphorus oxychloride and 450 g of butadiene are mixed under dry nitrogen at −20° C and the resulting mixture is introduced into an enamelled stirrer-equipped autoclave. After the autoclave has been closed, the mixture is heated to 50° C and left at that temperature for 73 hours. Thereafter, the liquid fraction, consisting predominantly of phosphorus oxychloride together with residues of methyl dichlorophosphine and butadiene dissolved therein, is allowed to drain off from solid crystalline 1-methyl-1,1-dichlorphospholine. A further quantity of these substances is obtained by evacuating the reactor and condensing the vapors escaping. A total of 2138 g of phosphorus oxychloride (94.6% of the input) and 23 g of methyl dichlorophosphine (2.3% of the input) are recovered. 1230 g of aceticanhydride are added to the residue of 1-methyl-1,1-dichlorophospholine, the mixture is slowly heated to 90° C and left at that temperature for 4 hours. Acetyl chloride is removed through an attached column. The further working up of acetyl chloride, aceticanhydride and 1-methyl-1-oxophospholine is carried out in the same way as in Example 7. A total of 883 g of acetyl chloride (93.8% of the theoretical yield), 575 g of aceticanhydride (93% of the theoretical yield) and 510 g of 1-methyl-1-oxophospholine (75.5% of the theoretical yield) is obtained. The acetyl chloride is found to contain 21 ppm of phosphorus.

EXAMPLE 9

The reaction sequence, including working up, described in Example 2 is repeated with 262 g of ethyl dichlorophosphine instead of methyl dichlorophospholine. The yield of 1-ethyl-3-methyl-1-oxophospholine amounts to 141 g (49% of the theoretical yield).

EXAMPLE 10

The reaction sequence, including working up, described in Example 2 is repeated with 358 g of phenyl dichlorophosphine instead of methyl dichlorophosphine. The yield of 1-phenyl-3-methyl-1-oxophospholine amounts to 177 g (46% of the theoretical yield).

It will be appreciated that the instant specification and examples are set forth by way of illustration and not limitation, and that various modifications and changes may be made without departing from the spirit and scope of the present invention.

What is claimed is:

1. In the production of isomeric five-membered ring cyclic unsaturated phosphine dichlorides by reacting an organophosphorus dichloride with a diene, the improvement which comprises carrying out the reaction in a carboxylic acid chloride.

2. A process as claimed in claim 1, wherein the carboxylic acid chloride is the chloride of at least one acid selected from the group consisting of an optionally halogen-substituted alkane carboxylic acid having up to 4 carbon atoms, an aromatic carboxylic acid optionally substituted by at least one of alkyl of up to 4 carbon atoms and halogen and an aralkane carboxylic acid having up to 4 carbon atoms in the alkane moiety and optionally substituted by at least one of halogen and alkyl of up to 4 carbon atoms.

3. A process as claimed in claim 1, wherein the organophosphorus dichloride is methyl dichlorophosphine, ethyl dichlorophosphine or phenyl dichlorophosphine.

4. A process as claimed in claim 1, wherein the diene is butadiene, isoprene, 2,3-dimethyl butadiene or chloroprene.

5. A process as claimed in claim 1, wherein the carboxylic acid chloride is acetyl chloride.

6. A process as claimed in claim 1, wherein the reaction is effected in the presence of a polymerization inhibitor.

7. A process as claimed in claim 2, wherein the organophosphorus dichloride is methyl dichlorophosphine, ethyl dichlorophosphine or phenyl dichlorophosphine, the diene is butadiene, isoprene, 2,3-dimethyl butadiene or chloroprene, the carboxylic acid chloride is acetyl chloride and the reaction is effected in the presence of a polymerization inhibitor.

* * * * *